United States Patent [19]
Törnblom

[11] 3,944,911
[45] Mar. 16, 1976

[54] APPARATUS FOR MAGNETICALLY DETECTING FAULTS IN METAL BODIES UTILIZING A MULTIPHASE GENERATOR TO GENERATE A ROTATING FIELD IN THE BODY

[75] Inventor: Bengt Hj. Törnblom, Vasteras, Sweden

[73] Assignee: Allmanna Svenska Elektriska Aktiebolaget, Vasteras, Sweden

[22] Filed: June 18, 1974

[21] Appl. No.: 480,424

[30] Foreign Application Priority Data
June 21, 1973  Sweden .............................. 7308786

[52] U.S. Cl. .................................... 324/37; 324/40
[51] Int. Cl.² ......................................... G01R 33/12
[58] Field of Search ....................... 324/37, 40, 34 E

[56] References Cited
UNITED STATES PATENTS
2,467,306  4/1949  Habig .................................... 324/40

FOREIGN PATENTS OR APPLICATIONS
847,661  6/1952  Germany .............................. 324/37
742,535  5/1943  Germany .............................. 324/37

*Primary Examiner*—Robert J. Corcoran
*Attorney, Agent, or Firm*—Kenyon & Kenyon Reilly Carr & Chapin

[57] ABSTRACT

An improved device for magnetically detecting and locating defects in metal bodies such as shafts, tubes, strips, sheets etc., in which a multiphase generator is used to generate a traveling field such as a rotating or linearly traveling field in the body being tested and in which means are provided to sense any assymetry in the resulting magnetic field resulting from eddy currents induced in the object such as to permit determining the location and nature of the fault from the electrical signals obtained.

1 Claim, 9 Drawing Figures

APPARATUS FOR MAGNETICALLY DETECTING FAULTS IN METAL BODIES UTILIZING A MULTIPHASE GENERATOR TO GENERATE A ROTATING FIELD IN THE BODY

BACKGROUND OF THE INVENTION

This invention relates to magnetic apparatus for the testing of metal bodies such as shafts, tubes, strips, etc., to detect and locate defects therein in general, and more particularly to an improved device of this nature which induces a traveling field such as a rotating field in the test piece.

Devices of the type which induce eddy currents in a metal test object, often in connection with a relative motion between the device for testing and the transducer of the device, are known. With a device of this nature, a fault in the test piece will result in an alteration of propagation of the eddy current. This fault can then be electrically detected to provide an appropriate output indicating the presence of a fault. Althrough these devices operate well under some circumstances, they suffer from certain disadvantages. Very often, the direction of relative movement between the device transducer and the test piece is in a direction parallel to the longitudinal axis of the test piece, particularly when this piece is a rod, drive shaft, or the like. As a result the sensitivity to measurement is not always as high as its desired. This is particularly true in the axial direction. However, objects of this nature very often have faults which have an axial extension. Thus, such faults only disturb the field a small amount and can pass by undetected.

In view of this, it is clear that there is a need for improved apparatus which is more sensitive to all types of faults and also which can provide additional information regarding the type and location of the fault.

SUMMARY OF THE INVENTION

In its broadest sense, the present invention includes inducing a traveling field into the object under test and detecting assymetries resulting from faults. The traveling field may, for example, be a rotating field which type field is particularly useful when testing cylindrical objects. As the field is rotated, as long as no faults are detected, symetry of the multiphase rotating field will exist. A fault, however, will result in disturbing the symetry which disturbance can be detected to provide an appropriate output.

In the simplest embodiment, a multiphase generator, typically a three-phase generator, is coupled to an input transducer including one coil per phase. The coils are symetrically placed around the body under test and, when fed by the multiphase generator, convey fluxes through the test object. As the field rotates, any faults or irregularities in the body such as cracks, indentations, segrations, blisters and so on, will cause an assymetry in the electrical circuit. In this embodiment, the assymetry is detected by detecting a voltage difference between the neutral point of the generator and the neutral point of the transducer coil. In a second embodiment, two sets of coils are provided, one coupled to the generator for inducing eddy currents in the test object and a second set of coils similarly arranged for detecting these eddy currents. The detector transducer is coupled in a bridge arrangement to a balanced impedance arrangement and faults detected by detecting an unbalance between the netrual of the pickup transducer coils and the neutral of the impedance arrangement. Other arrangements are shown in which a pair of rotating fields are induced in the test object and in which pickup transducers arranged in bridge circuits are provided for the purposes of detection. In a final embodiment, a single detection coil having a differential output which may then be amplified is illustrated.

Through the rotating field of the present invention the fluxes generated have a motion relative the test object and thus, the test object can remain stationary with respect to the testing device. In other words, it is not necessary to provide a physical relative movement between the testing device and the test object. In addition, it is possible to obtain a flux traveling around a cross section of the shaft. As a result, the sensitivity of the measuring device is increased making it able to detect faults which might have gone unnoticed in prior art devices and also making it possible to detect fault location more accurately, i.e., it will be evident to those skilled in the art that appropriate apparatus can be constructed, to utilize the input phase to determine the exact location of a fault.

DETAILED DESCRIPTION OF THE PREFERRED EMBODIMENT

Figure 1:
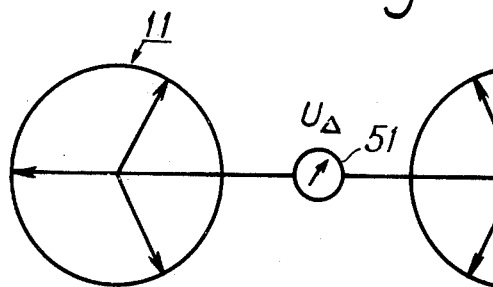
FIG. 1 is a schematic-vector diagram illustrating the principle of the present invention.
Figure 1A:
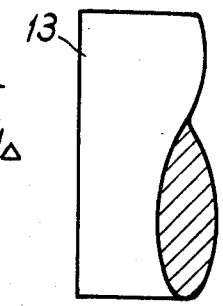
FIG. 1A illustrates a test object such as a shaft which may be tested using the arrangement of FIG. 1.

FIGS. 1 and 1A illustrate the basic principle upon which the present invention rests. At the outset, it should be noted that although the examples all deal with a three phase rotating field, other arrangements are possible. Basically, the invention requires generating a traveling field using two or more phases. Thus, rather than generating a rotating field, a linearly traveling field such as those used in conjunction with linear motors is also possible. In each case, means are provided to detect any irregularity by detecting assymetry in the field. As will become evident below, this may be done by detecting an assymetry in the transducer coils inducing the rotating field into the object. It is well known that the effect of the induced eddy currents on the coils causing these eddy currents will result in electrical variations if the eddy currents are not symetrical due to an irregularity. Thus, the transducer used to generate these currents may be used as part of the detection circuit. Similarly, separate detection coils may be used.

FIG. 1 illustrates a system in which a three-phase generator 11 having the vectors shown is used to drive a transducer 12 arranged about a test object such as the shaft 13 illustrated on FIG. 1A. The rotating flux illustrated by the vectors of the transducer 12 will remain balanced as long as no irregularities are encountered. However, when an irregularity is encountered, the phase and magnitude of one of the vectors such as a vector 14 will be affected. This assymetry caused by the fault will be reflected back to the coil. The fault can be detected by measuring the voltage $U_\Delta$ between the neutral point of the generator 11 and the neutral point of the transducer arrangement 13 using up an appropriate meter 51. This voltage $U_\Delta$ is shown on the vector diagram associated with the transducer 12. That is, it will be the difference in voltage which, when added to the vector 14 will result in the vector 53 which would have been obtained without disturbance.

Figure 2:
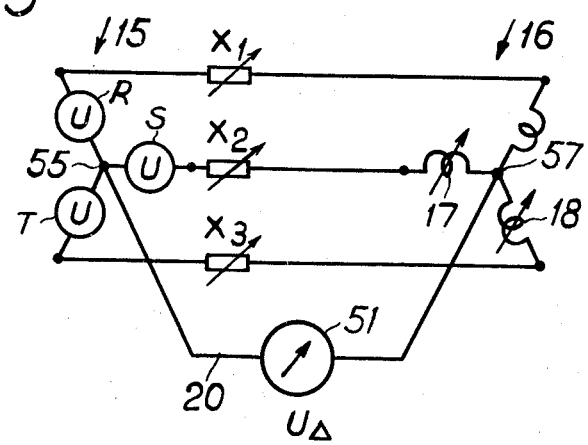
FIG. 2 is a schematic of apparatus for achieving the rotating fields illustrated by FIG. 1.

FIG. 2 illustrates a first embodiment for implementing the concept illustrated by FIG. 1. A conventional threephase generator 15 having the phases R, S and T is provided with the generator in a Y or star configuration. The neutral point 55 of the generator 15 may, if desired, be grounded. Although in most cases a sinusoidal generator is preferable, it should be recognized that pulse generators, triangular wave generators and so on may also be used in the present invention. Also, although a single three-phase generator is illustrated, it should also be recognized that three separate generators properly synchronized and coupled togehter in a Y configuration can equally well be used. The generator outputs are coupled to three coils 16, 17 and 18 which are also in a Y configuration. The neutral point 57 of the coils 16, 17 and 18 cannot be grounded but must be floating with respect to the neutral point 55 of the generator. As shown, the phase R is coupled through a variable impedance X1 to the coil 16, the phase S through a variable impedance X2 to the coil 17 and the phase T through a variable impedance X3 to the coil 18. In a circuit 20 between the neutral 55 and the neutral 57 the meter 51 is placed to detect any unbalance in the manner described above.

Figure 2A:
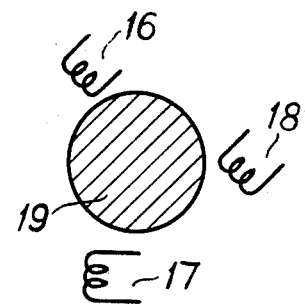
FIG. 2A illustrates the coil arrangement for the transducer coil of FIG. 1.

The physical arrangements of the coils 16, 17 and 18 is illustrated on FIG. 2A showing coils arranged about an object an object 19 such as a rod which is to be tested. As illustrated, the coils are placed around the test object 19 with a mutual angle between the coils of 360 divided by N where N is the number of phases. Thus, in the example of FIGS. 2 and 2A, the angular spacing between coils is 60°. With this arrangement shown on FIGS. 2 and 2A, a rotating field perpendicular to the axis of the shaft or rod 19 results. If, rather than inducing a rotating field it is desired to induce a linearly traveling field in an object, then the coils will be placed along two parallel lines aside the object such in the way the coils are placed for a linear motor.

The differential signal $U_\Delta$ measured at the meter 51 can be evaluated both as to magnitude and phase relative to the reference generator 11. The amplitude is related to the magnitude of the fault and the phase relative to the generator will indicate the fault location. for such measurements, conventional voltmeters and phase angle meters may be used. As noted, relative motion is obtained without movement of the object. However, it is preferable that the shaft 19 be supported for movement in the longitudinal direction so that all portions of the shaft can be examined to determine the presence of absence of faults therein.

Although balance circuits are used, these circuits do not have to be absolutely balanced in all cases. In some instances a certain unbalance may be required to accentuate possible faults. Thus, what is referred to as balancing herein should be considered relative rather than an absolute balancing. The system uses dynamic control since in contrast to prior art devices, the transducers themselves generate the movement of the flux relative to the test object. In addition, the rotating field provides a phase vector to which the fault is added permitting detection of the phase and thus the location of the fault.

The impedance elements X1, X2 and X3 of FIG. 2 are variable so that the circuit may be balanced before the beginning of test with a known object containing no faults inserted between the coils. In addition, two of the phase coils 17 and 18 are adjustable to provide for further trimming. As a result, through these two types of adjustment, a completely balanced symetrical arrangement can be preestablished before testing. Once set up, the system is operated with a test object 19 in place as shown. Any faults encountered will be indicated by a voltage U in the neutral branch 20 in the manner described above. Irregularities in the field image detected by this apparatus can be detected in regard to amplitude and phase as noted above and also with respect to frequency, i.e., it is possible to operate the generator 15 at different frequencies to obtain further information regarding the faults. Although the transducer 16 need not have the same number of legs or phrases as the generator 15, such is normally preferred.

Figure 3:
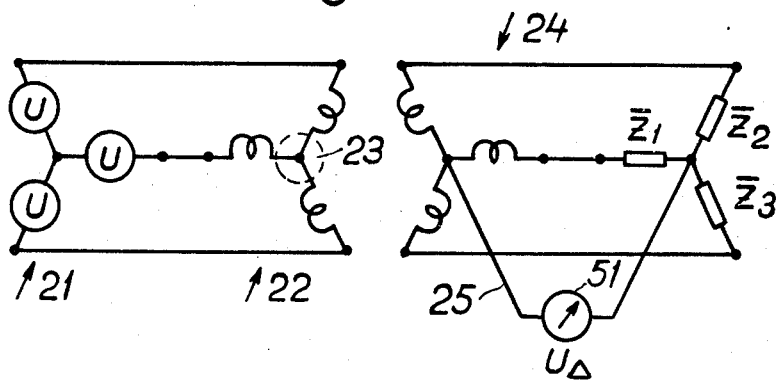
FIG. 3 illustrates a similar arrangement in which separate transudcer induction and pickup coils are used.

FIG. 3 illustrates a further embodiment of the invention. Here there is provided a multiphase generator 21 driving a transducer coil arrangement 22 arranged about a test object 23. In this case, however, rather than using the neutral branch between the generator 21 and transducer coil arrangement 22, an additional transducer arrangement 24 is provided, also in a Y configuration. The pickup transducer coils 24 are coupled in a bridge circuit with impedance designated Z1, Z2 and Z3. The output indication of the voltage $U_\Delta$ is obtained from the neutral branch 25 of the bridge arrangement. That is, the meter 51 is connected between the neutral point of the Y connected coils 24 and the Y connected impedances Z1, Z2 and Z3. It is, of course, possible to add further links in a balanced chain such as that of FIG. 3, i.e., additional links similar to that made up of the coils 24 in the impedances Z1, Z2 and Z3 can be added and the voltage detected in the zero branch of that link. In any case, however, the principle of operation is the same, i.e., faults are detected using a moving field.

Figure 4:
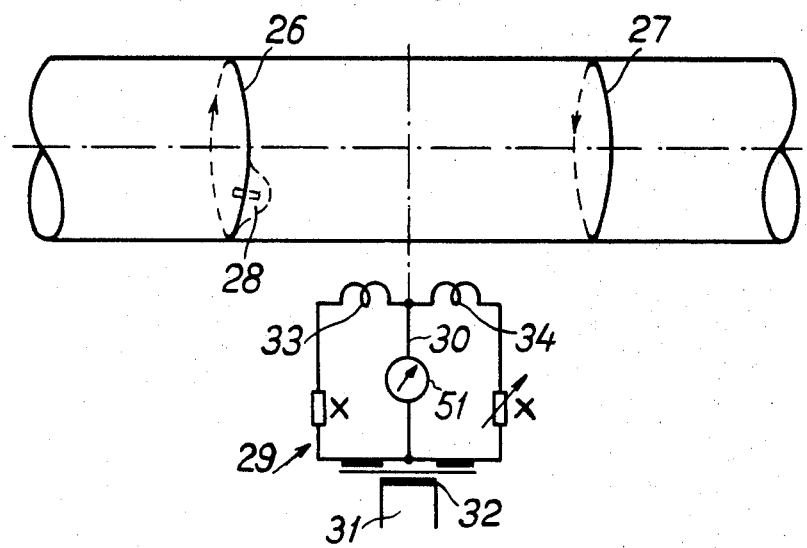
FIG. 4 illustrates an arrangement in which two rotating fields are induced in the test object and faults detected using a pair of transducers in a bridge circuit.

A further embodiment of the invention is illustrated by FIG. 4. Here, two rotating fields 26 and 27 are induced using arrangements such as that of FIG. 2. The coils such as the coils 16, 17 and 18 of FIG. 2A used to induce these rotating fields are not shown for sake of simplicity. The coils used to generate the rotating fields 26 and 27 may be supplied by separate generators or may be supplied from a common generator. For purposes of detection, pickup transducer coils 33 and 34 arranged in a bridge circuit are provided. The coils 33 and 34 are connected together on one side and have their other sides taken respectively through impedances X to two secondary windings of a transformer 32.

The primary 31 of the transformer has a generator voltage induced thereon. At least one of the impedances X is variable as shown for balancing the detector arrangement indicated generally as 29. In this case, the voltage is measured in the branch 30 between the junction point of the transducer coils 33 and 34 and the center tap of the secondary of the transformer 32. As before, an appropriate meter or the like 51 is provided. Without any irregularities in the test object, the bridge 29 will remain balanced with equal amounts of current being induced from the rotating fields. However, if an irregularity such as an irregularity 28 is encountered, the flux will be distorted resulting in a variation at the transducer coil 33, for example, which will cause an unbalanced condition which will be detected by the meter 51. The fields can be in the same or opposite directions. This applies to the direction of the windings as well as the direction of movement. As with the other embodiments, the permability of the fault along with the coupling factor of the transducer provides sufficient latitude for evaluating and classifying results. These variables along with the above mentioned frequency modulation of the moving field and in addition automatic balancing can be included in a complete system.

With arrangements such as that of FIG. 4, additional transducer arrangements can be provided with two or more generators used, each connected to a separate transducer and the transducers placed at different portions of the test body either secured thereto or in a movable fashion. Assymetries can be examined for each separate transducer or for transducer mutually, similar to the manner described in connection with FIG. 4. As noted above, it is also possible for a single generator to be used for driving a plurality of transducers.

Figure 5:
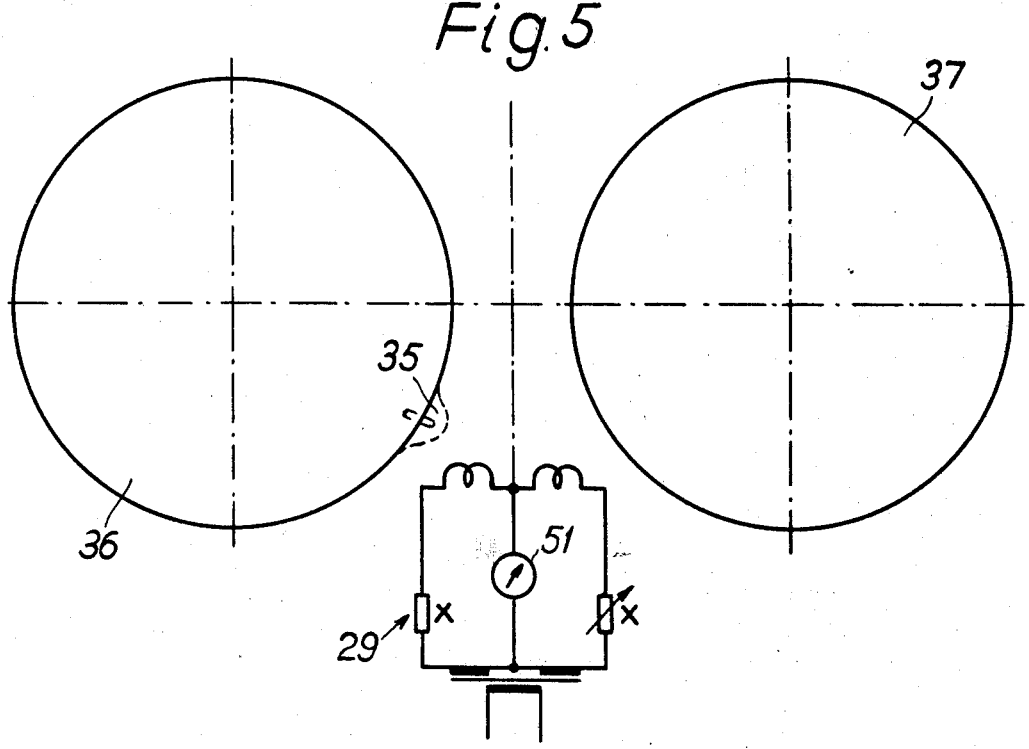
FIG. 5 illustrates a similar arrangement with the rotating fields induced in a planar rather than a cylindrical test object.

FIG. 5 shows an alternate form of the arrangement of FIG. 4 for detecting faults in a planar body such as a sheet of metal. In this arrangement, the coils are arranged to induce rotating fields which rotate in the planar surface. The detector arrangement 29 is exactly as described above. Thus, there are shown two rotating fields 36 and 37 rotating in the plane of a planer test object. If a fault such as a fault 35 is detected, field distortion will occur resulting in an unbalance in the detector circuit 29 which will result in a reading on the meter 51.

Figure 6:
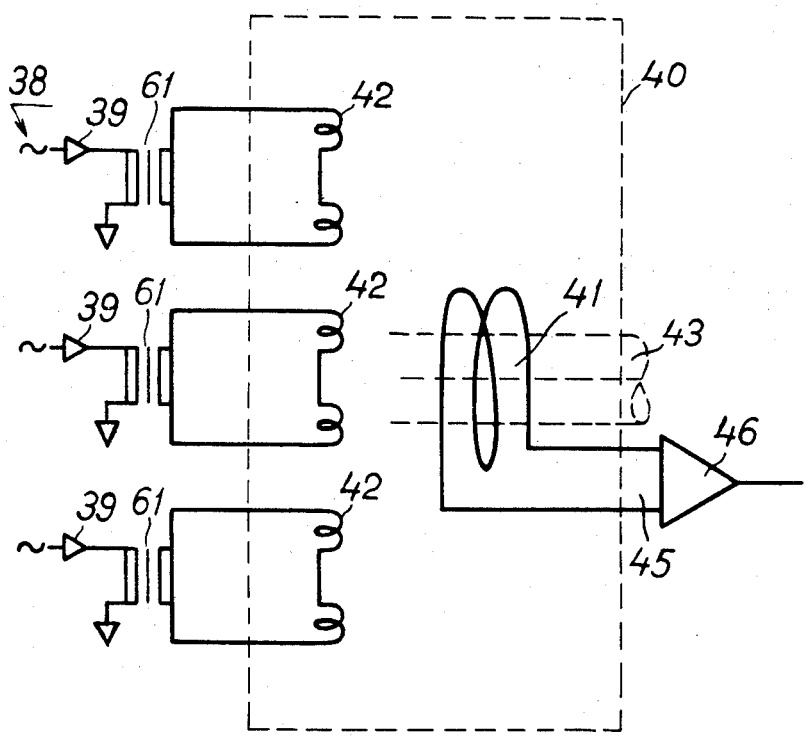
FIG. 6 is a schematic illustration illustrating an arrangement where the output transducer is a single differential coil providing its output to a differential amplifier.
Figure 7:
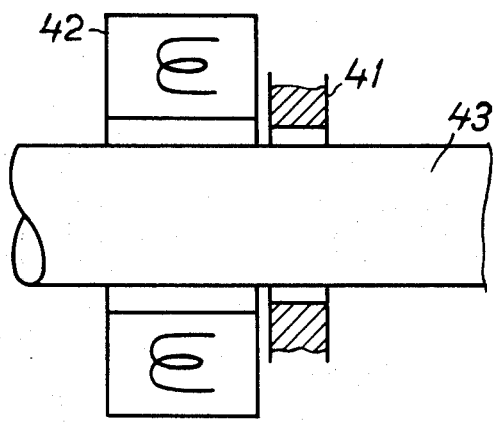
FIG. 7 is a mechanical schematic illustrating the coil arrangement for the embodiment of FIG. 6.

FIGS. 6 and 7 illustrate a further alternative embodiment of the invention. FIG. 6 is an electrical schematic and FIG. 7 a mechanical schematic of the arrangement. An appropriate generator provides three phase current indicated schematically by 38 to three amplifiers 39 each of which is coupled to the primary of a transformer 61. The secondary of each of the transformers 61 is coupled to a transducer coil 42. The transducer coils 47 will be spaced around the test object 43 much in the same manner described above in connection with FIG. 2A. This arrangement is illustrated schematically on FIG. 7. Adjacent the primary transducer circuit made up of the coils 42 is a secondary transducer coil 41. Its location relative to the coils 42 is illustrated on FIG. 7. Coil 41 comprises a single differential coil and provides an output at 45 which may then be provided to a differential amplifier 46 or the like for further amplification. The signal so obtained may then be provided to a meter or other evaluation circuits.

In the arrangement shown on FIG. 6, the secondary coil 41 is immediately adjacent the primary coil arrangement 42. This is not an absolute necessity and in some cases the coil 41 may be positioned inside the primary coil 42. Also although shown as a single phase differential coil, it is possible to use two or more coils in the secondary circuit and combine them in appropriate fashion. These and other modifications may be made without departing from the spirit of the invention which is intended to be limited solely by the appended claims.

What is claimed is:

1. Apparatus for testing metal bodies comprising:
  a. a first y-connected multi-phase generator;
  b. a first plurality of y-connected transducer coils comprising at least one coil per phase of the multi-phase generator arranged symmetrically relative to a metal body to be tested, said coils coupled to the phase outputs of said generator such as to induce a moving field in said body when fed with a multi-phase current therefrom; and
  c. a second plurality of y-connected transducer coils comprising at least one coil per phase of the multi-phase generator arranged symmetrical relative to said metal body to be tested, said coils coupled to the phase outputs of said generator such as to induce a moving field in said body whose direction is opposite to that of the moving field generated by said first plurality of y-connected transducer coils when fed with a multi-phase current from said multi-phase generator, said second plurality of y-connected transducer coils being located at a section of said metal body different from the section where said first plurality of y-connected transducer coils are located; and
  d. means to detect variations in the electrical field generated by said transducer coils which occur when faults and irregularities in the body being tested are encountered comprising
   1. First and second transducer coils located adjacent to said metal body between said first and second pluralities of transducer coils and connected in series;
   2. a transformer having first and second secondary windings in series and a single primary winding;
   3. first and second impedances coupling said first and second transducer coils in series to said first and second secondary windings in series;
   4. means to detect an unbalance between the point at which said first and second transducer coils are connected in series and the point at which said first and second secondaries are connected in series; and
   5. means to induce a voltage on the primary of said transformer.

* * * * *